(12) United States Patent
Hawke et al.

(10) Patent No.: US 9,265,412 B2
(45) Date of Patent: Feb. 23, 2016

(54) MEANS AND METHOD FOR DEMONSTRATING THE EFFECTS OF LOW CYLINDER ASTIGMATISM CORRECTION

(71) Applicant: Johnson & Johnson Vision Care, Inc., Jacksonville, FL (US)

(72) Inventors: Ryan Hawke, Jacksonville, FL (US); Jonathan Hansen, Jacksonville, FL (US); Ross Franklin, The Gap (AU); Andy Milton, Woodhead Drive (GB); Ben Rose, Royston (GB); Michael Murphy, Cambridge (GB)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 60 days.

(21) Appl. No.: 14/011,131

(22) Filed: Aug. 27, 2013

(65) Prior Publication Data

US 2015/0062535 A1    Mar. 5, 2015

(51) Int. Cl.
*A61B 3/02* (2006.01)
*A61B 3/028* (2006.01)
*A61B 3/032* (2006.01)
*A61B 3/036* (2006.01)

(52) U.S. Cl.
CPC . *A61B 3/02* (2013.01); *A61B 3/028* (2013.01); *A61B 3/032* (2013.01); *A61B 3/036* (2013.01)

(58) Field of Classification Search
CPC .......... A61B 3/02; A61B 3/022; A61B 3/028; A61B 3/036; A61B 3/0058; A61B 3/0091; A61B 3/032; A61B 3/0285
See application file for complete search history.

(56) References Cited

U.S. PATENT DOCUMENTS

| | | | |
|---|---|---|---|
| 1,369,136 A * | 2/1921 | Shigon | 351/241 |
| 2,385,992 A | 5/1944 | Jobe | |
| 3,874,774 A * | 4/1975 | Humphrey | 351/233 |
| 3,955,564 A * | 5/1976 | Levinson et al. | 606/204.25 |
| 4,365,873 A | 12/1982 | Ginsburg | |
| 4,415,243 A | 11/1983 | Gottlob et al. | |
| 4,611,893 A | 9/1986 | Schrier | |
| 4,615,594 A | 10/1986 | Task | |
| 4,789,234 A | 12/1988 | Ginsburg et al. | |
| 4,943,162 A * | 7/1990 | Sims | 351/235 |
| 5,054,908 A | 10/1991 | Katsumi et al. | |
| 5,675,399 A | 10/1997 | Kohayakawa | |
| 6,142,631 A | 11/2000 | Murdoch et al. | |

(Continued)

FOREIGN PATENT DOCUMENTS

| | | |
|---|---|---|
| EP | 1470777 A1 | 10/2004 |
| WO | WO 92/10970 A1 | 7/1992 |
| WO | WO 02/00105 A1 | 1/2002 |

OTHER PUBLICATIONS

Currie, Z, et al, "Reliability of Snellen Charts for Testing Visual Acuity for Driving: Prospective Study and Postal Questionnaire", http://lib.bioinfo.pl/mid:11039964, uploaded Jul. 10, 2013.

(Continued)

*Primary Examiner* — Jordan Schwartz
(74) *Attorney, Agent, or Firm* — Carl J. Evens (57) ABSTRACT

A new vision test, incorporating textual and non-textual elements in an image, is configured to demonstrate the effects of low cylinder astigmatism and other sources of blur on visual quality. The elements are designed to be noticeable, relevant, important and engaging. The new vision test may be utilized to supplement conventional vision testing.

1 Claim, 11 Drawing Sheets

(56) References Cited

U.S. PATENT DOCUMENTS

| | | |
|---|---|---|
| 6,379,007 B1 | 4/2002 | Farb |
| 7,391,504 B1 | 6/2008 | Pinkus et al. |
| 7,524,065 B1 | 4/2009 | Ogilvie |
| 2005/0152675 A1 | 7/2005 | Hanes |
| 2006/0152675 A1 | 7/2006 | Toshima |
| 2007/0195264 A1 | 8/2007 | Lai |
| 2013/0301007 A1* | 11/2013 | Wolffsohn et al. ............ 351/239 |

OTHER PUBLICATIONS

Kaiser, P. K., "Prospective Evaluation of Visual Acuity Assessment: A Comparison of Snellen Versus ETDRS Charts in Clinical Practice (an AOS Thesis)", Transactions of the American Ophthalmological Society, http://www.nibi.nlm=.nih.gov/pmc/articles/PMC2814576, Jul 10, 2013.

"Snellen Chart—Definition", http://www.wordiq.comdefinition/Snellen_chart Jul. 10, 2013.

Written Opinion by the Intellectual Property Office of Singapore for Application No. 10201400372X dated Dec. 15, 2014.

European Search Report for corresponding Application No. EP14159621 dated Jan. 9, 2015.

* cited by examiner

| Random | Wording |
|---|---|
| Text | Text |
| Text | Text |
| Text | Text |
| Text | Text |
| Text | Text |
| Text | Text |
| Text | Text |
| Text | Text |
| Text | Text |
| Text | Text |
| Text | Text |
| Text | Text |
| Text | Text |
| Text | Text |
| Text | Text |
| Text | Text |
| Text | Text |
| Text | Text |

READ THE FOLLOWING

| Random | Wording |
| Text Text | Text Text Text |
| Text Text | Text Text Text |
| Text Text | Text Text Text |
| Text Text | Text Text Text |
| Text Text | Text Text |

MEANS AND METHOD FOR DEMONSTRATING THE EFFECTS OF LOW CYLINDER ASTIGMATISM CORRECTION

BACKGROUND OF THE INVENTION

1. Field of the Invention

The present invention relates to human vision testing devices and methods, and more particularly to a vision test chart and/or series of vision test charts and associated test methodology that may be utilized to both assess and demonstrate the effect of blur reduction through optical correction, such as low cylinder astigmatism or high order aberrations correction, on visual quality.

2. Discussion of the Related Art

Visual acuity charts, such as Snellen charts, are the most widely utilized form of vision test in clinical practice. Standard visual acuity tests require that a patient identify letters of the alphabet of decreasing size from a predetermined position or distance. The smallest row of letters that may be read accurately indicates the patient's visual acuity.

The symbols on any acuity chart are known as optotypes. In a Snellen chart, the optotypes are designed as block letters with a particular geometry. Many modern visual acuity charts use a Sloan optotype, where the thickness of the lines equals the thickness of the white spaces between lines and the thickness of the gap in the letter "C". The height and width of the optotype is five (5) times the thickness of the line.

During a standard eye exam, the visual acuity chart is often the only visual target for the patient to assess changes in the quality of vision correction with different levels of correction. Due to the fixed contrast, limited range of spatial frequencies, and lack of imagery, the visual acuity chart cannot demonstrate the real world vision quality that the patient will experience. Research into the subjective quality of images based on optical properties has shown that spatial frequencies which are lower than the usual threshold measured on a visual acuity chart are the most important aspect of the perceived quality of an image.

In addition to the simplicity of the content, the letters on a visual acuity chart are an incomplete representation of the visual stimuli an individual both experiences and sees in a typical day. The best representation the visual acuity chart gives is of the ability to read distant signs, but there are many other visual experiences in an individual's life. These experiences include reading and recognizing faces, seeing textures, trying to make out an object that may be partially obscured, and more.

In astigmatism, differential curvature in the optics of the eye causes the image to be blurred rather than focusing to a point. The amount and shape of the blur differs with each patient's prescription and/or particular condition. Higher levels of astigmatism are very noticeable and the benefit of its correction is clearly demonstrated by looking at a visual acuity chart. Low levels of astigmatism are not as noticeable to the individual, particularly when being assessed with a standard eye chart tests as described above, as these tests do not always provide a compelling demonstration of low level cylinder correction for treating astigmatism. When the patient is being fit for contact lenses, this often leads to practitioners choosing to fit astigmatic patients into spherical contact lenses. This is primarily due to a lack of perceived visual benefit of a toric contact lens that uses cylinder to correct astigmatic blur from both the practioner's and patient's perspective. The consequence of fitting an astigmatic patient into a spherical contact lens is reduced vision quality as compared to that which may be achieved by utilizing a lens for correcting the low cylinder astigmatism. Accordingly, there is a need for an eye test that demonstrates the benefit of correcting low cylinder astigmatism or other causes of blur.

In addition to blur caused by low levels of astigmatism, blur from other sources are less noticeable using a visual acuity chart than in everyday life. These sources include blur from multifocal corrective lenses, spherical aberration, and other high order aberrations. An eye test that demonstrates real world vision improvements may be utilized to help a patient choose the best multifocal design for them or decide on the benefit of correcting high order aberrations, all without leaving the office.

SUMMARY OF THE INVENTION

The means and method of the present invention for demonstrating the effects of blur reduction through optical correction, such as the correction of low cylinder astigmatism or high order aberrations, overcome the disadvantages associated with the prior art as briefly set forth above.

The present invention is directed to a method and means for demonstrating the effect and benefit of low cylinder astigmatism correction and other optical corrections. Typically, a patient or individual with low levels of astigmatism will not appreciate the impact of correcting for the astigmatism based on standard visual acuity charts. Accordingly, the present invention utilizes an eye chart and test designed specifically to demonstrate the power or effect of low cylinder astigmatism correction. The chart and test are designed to utilize a knowledge of the patient, a knowledge of the optics and a knowledge of visual perception in a more meaningful and impactful fashion. More specifically, the eyes (optics) view a target and the image is blurred due to astigmatism, the brain interprets the image (visual perception) and the patient decides if the visual difference makes it worthwhile to try toric lenses to correct for cylinder. Accordingly, the eye chart and test examines the optics aspect to determine which targets maximize the impact of a low cylinder correction, visual perception to determine how can one leverage the perceptual aspects of vision, and finally the patient to determine how to make the difference meaningful and relevant. With respect to the optics, the chart or scene comprises images that include high frequency elements and low contrast elements, for example, text, in the context of real world signage and surface textures. With respect to visual perception, the chart or scene comprises images that include facial expressions, perspective and distraction, for example, a real world street setting with depth including people walking and signage with text overlaid on distracting backgrounds. With respect to the patient, the components of the chart or scene combine to provide a noticeable, relevant, important and engaging improvement in vision when shown the correction for low astigmatism when compared to a spherical correction. The visual change of image components as described are not limited to astigmatic blur. These same components will perceptibly change with blur caused by myopic or hyperopic error, blur from multifocal correction and high order aberrations. While initially targeted at demonstrating the benefit of correcting low levels of astigmatism, the present invention's benefit extends to these and other forms of optical blur correction or comparison as well.

The vision test chart and method of the present invention is easy to utilize, engaging, and most importantly, powerfully demonstrates the difference low cylinder astigmatism correction may make in an individual's everyday life. The process adds minimal time to a standard eye exam and provides the opportunity for a patient to see what it is like to see more clearly in a real world situation, or as close to a real world situation that is possible in a controlled environment. The eye exam itself may be accomplished with a simple flipper tool and an image or scene in accordance with the present invention. In addition, the present invention enables improved patient education on the visual impact of astigmatism due to the more compelling demonstration compared to the traditional practice of utilizing existing visual acuity charts.

The vision test chart and method of the present invention may be utilized alone or in combination with any other visual acuity tests. For example, the vision test chart and method of the present invention may be utilized in combination with the standard visual acuity chart. Alternatively, the vision test chart and method of the present invention may be utilized as a stand-alone test, because elements within the chart may be measureable or quantifiable as they relate to visual acuity, in addition to demonstrating the difference that blur correction makes.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
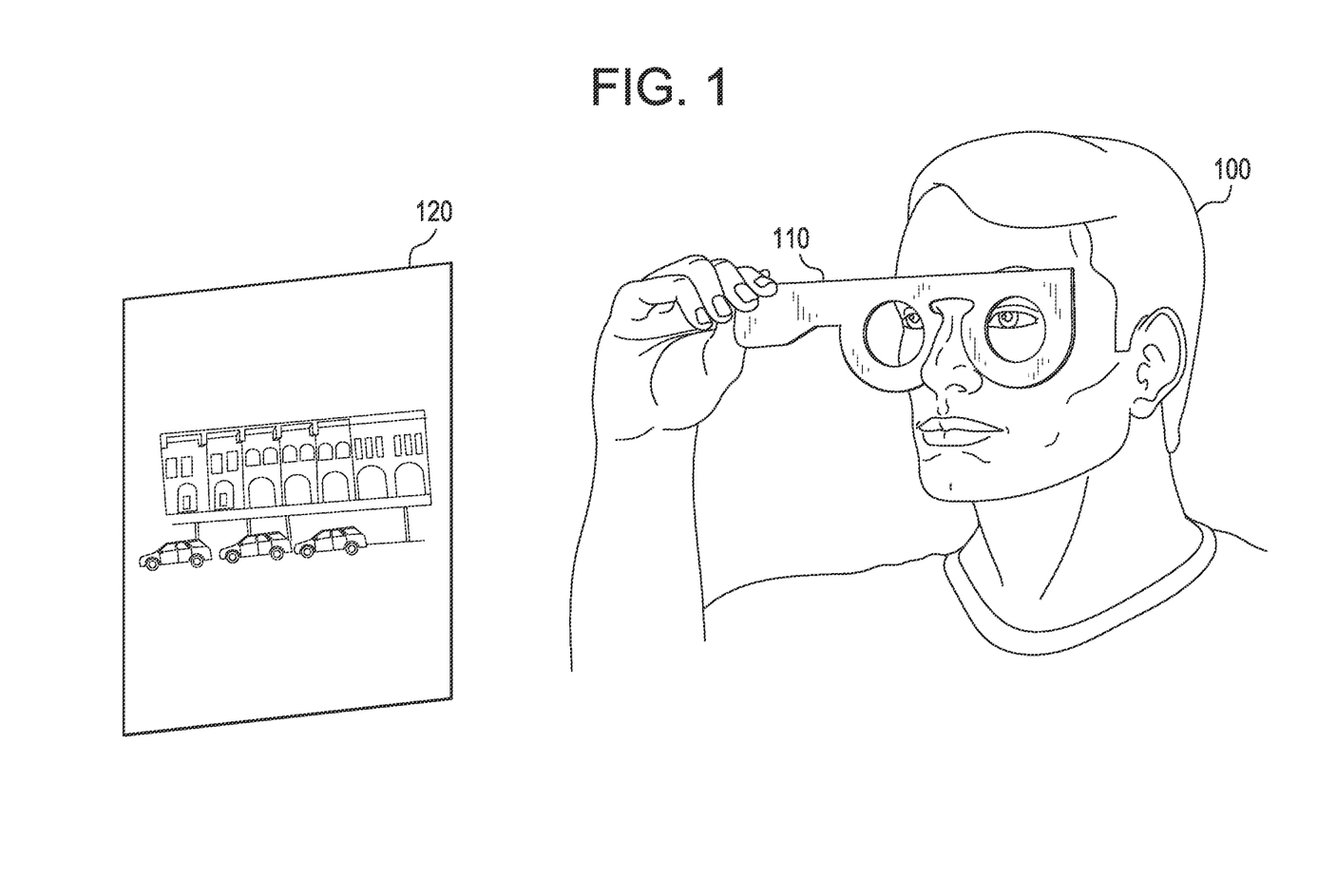
FIG. 1 is a diagrammatic representation of a patient undergoing an eye exam in accordance with the present invention.

The present invention is directed to a means and method for demonstrating the benefits and effects of low cylinder astigmatism correction, or blur from myopic or hyperopic error, presbyopic error and/or higher order aberrations. More specifically, an eye chart comprising a scene that includes elements that not only represent a real world image, but is also meaningful and relevant to the patient may be utilized to demonstrate the difference low cylinder astigmatism correction may make for an individual. The means and method of the present invention make use of a combination of meaningful patient elements, optic elements and visual perception elements in one or more scenes or images. Referring to FIG. 1, there is illustrated a patient 100 holding a simple flipper tool 110 while viewing a chart 120 in accordance with the present invention.

With respect to optics, how the eyes view an object or a scene, the key is to determine what targets or elements maximize the visual impact of low cylinder astigmatism correction. In general, targets or elements that are high frequency and which have low contrast maximize the impact of a low cylinder astigmatism correction. Low contrast features are more likely to become totally invisible in patients or individuals with uncorrected low level cylinder astigmatism; however, low contrast features may not necessarily give the greatest perception of a change with and without astigmatism correction. In other words, low contrast features that may be invisible through a low cylinder tend to be still quite difficult to see even with perfect correction. Accordingly, the high frequency features are also important. Within high frequency information, certain information proved to be of particular usefulness, including small text, for example, less than 0.9 mm from 40 cm and less than 14 mm at 6 m, gratings, for example, as utilized in contrast sensitivity function testing at greater than 20-30 cycles/degree, lines with edges and fine detail in images, for example, expression lines in faces or textures in natural images. While lines/edges are high frequency, they may not alone be particularly useful because the eye-brain system is especially sensitive to edges and lines. Accordingly, other elements should preferably be incorporated.

It is important to note that visual acuity and contrast sensitivity, as well as the impact optimal correction for these items may have, may vary significantly from patient to patient, even in patients with the same prescription. Accordingly, a target image or scene should preferably incorporate a range of orientations, frequencies/sizes, and contrast to demonstrate that low cylinder astigmatism correction makes a difference, and in some cases, a significant difference. Astigmatic blur is non-symmetric and, depending on prescription and patient, may have a larger impact on vertical, horizontal, or diagonal spatial frequencies. Including a range of orientations in the image is important to cover this range of patient prescriptions.

Individuals see with their eye and brain acting as a system, as the brain interprets the image, while the eyes are merely the optics. Accordingly, individuals may be comfortable with a certain amount of blur caused by astigmatism as the brain adapts to this blur. Therefore, it is more difficult to have an eye chart that leverages the perceptual aspects of vision. More specifically, there are a number of perceptual effects that work against a test designed to maximize the difference between no correction and low cylinder astigmatism correction. The brain may adapt to astigmatism blur and this effect may be particularly well developed if the individual has adapted to low cylinder astigmatism over an extended period of time. The brain is also very adept at filling in missing information in images based upon visual cues, previous experiences and best guesses. In addition, many of the classic visual illusions rely on the higher order interpretation of the image, and not on high frequency information, and therefore will not be disrupted by a low level of astigmatism. However, there are three (3) illusions that are affected by a low level of astigmatism; namely, hybrid images that combine high and low frequency elements, a combination of this hybrid approach with changing facial expressions, and images obscured behind a grating. There are perceptual effects that enhance the effect of low cylinder astigmatism correction; namely, motion/time and distraction. Moving text or images give the brain less time to fill in the missing information, and hence may be more difficult to interpret without optimal visual correction, in particular, low cylinder astigmatic correction. Similarly, an image or text may be flashed up for a brief period of time. A large amount of complex and superfluous visual information may distract the brain and make it more difficult to recognize familiar shapes and/or read text. Accordingly, perceptual aspects may be incorporated into the means and method of demonstrating the effects/benefits of low cylinder astigmatism correction to the patient in accordance with the present invention.

The individual makes a subjective decision as to whether he or she wants low cylinder astigmatism correction, based upon what they know and see. If the individual is not provided with the opportunity to see how much their vision may be improved, then any decision they make is being made with incomplete information. Accordingly, the present invention incorporates elements in an image that make the difference meaningful and relevant to the individual. To do this, the difference is preferably noticeable, important and engaging. In the noticeable category is magnitude of difference, binary behavior and obviousness. The magnitude of difference is essentially a measure of how big is the effect, is there an improvement in clarity, sharpness/contrast, and a change in how the overall image appears. The measurement of difference may have binary behavior, for example, absent or present, recognizable or not recognizable, and readable or not readable. This is measureable on a scale and quantifiable. Obviousness involves a determination of whether an individual can recognize the difference on his or her own or whether someone has to draw attention to the difference before it can be recognized. Under the important category is relevance, realism and consequence. With respect to relevance, the test content or scene is preferably relevant to the individual's daily life. With respect to realism, the test content or scene is preferably believable and realistic to the individual, such as the image looking substantially like a photograph of a place or location (i.e. natural). With respect to consequence, the test content or scene preferably has elements that have an effect on an aspect of daily life. Elements of this nature may include differences that are life threatening, for example, missing elements due to low cylinder astigmatism that may cause a car crash. The elements may also include differences that cause impairment, for example, missing elements due to low cylinder astigmatism may cause the individual not to be able to read a street sign. Under the engaging category is that the demonstration is interactive, educational, informative, interesting and surprising. These elements are self-explanatory.

Visual perception is a complex function and the present invention utilizes scenes and/or images that include elements that tend to show or emphasize a significant difference when present with a one (1) diopter cylinder correction. Given the right combination of elements in a scene and/or image, it may be possible to show a significant difference with a 0.75 diopter or lower levels of cylinder correction. In a preferred exemplary embodiment, an image or scene should comprise one or more of the following features: facial recognition and expressions, high frequency detail, gratings and text, rotating gratings, array of gratings, line drawings, text in motion, text in perspective, text with distraction and high contrast patterns.

It is important to note that the following text and corresponding figures illustrate individual aspects or components of a composite image that may be utilized in accordance with the present invention. An image in accordance with the present invention utilizes or comprises one or more of the exemplary components illustrated in FIGS. 2-11 to create a composite image that is preferably noticeable, relevant, important and engaging to the individual or patient undergoing testing. While FIG. 1 includes an exemplary eye chart, an image in accordance with the present invention would preferably look more like a photograph in substance and detail.

A composite image for facial recognition and expressions may be created utilizing low frequencies from one face and high frequencies from another face. This might involve images of two different people or two different facial expressions of the same person. A low cylinder eliminates the low contrast, high frequencies and changes the overall perception of the face and its expression. This is noticeable to the individual because the loss of high frequency information leads to an entirely different interpretation of the image (binary difference). For example, a scowling face may change to a more neutral face, or potentially one well known face could change into another. The former is easier to achieve in a more convincing way because the change required is smaller. This is important to the individual because the interpretation of facial expressions is highly relevant in everyday life. This is engaging to the individual because people are naturally drawn to pay attention to faces and facial expressions. The difference that correction makes, may result in an entirely different interpretation of the image, and may be surprising for the individual as well.

Figure 2:
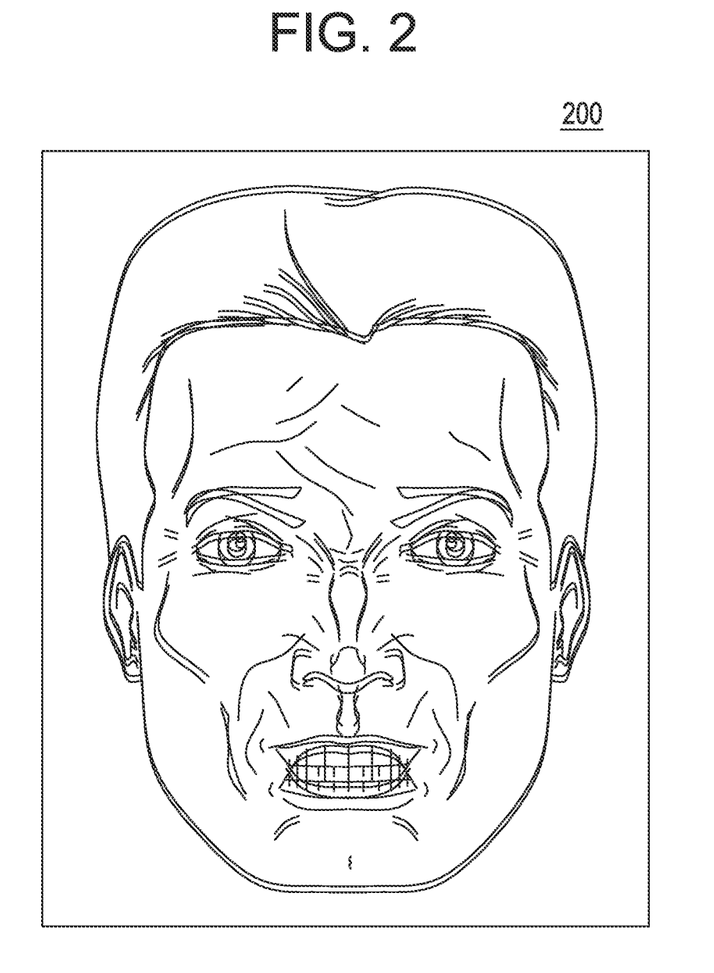
FIG. 2 is an exemplary facial expression composite in accordance with the present invention.

The above described effect may be achieved by passing one image through a high pass filter and overlaying this image on an image with a different facial expression. A composite image of a baby's face may offer a more fun version of the angry/calm composite, and thus it may increase the test's level of engagement. Another possible way to utilize the composite image principle in a more realistic way would be with an X-ray, which is high frequency and low contrast by nature. Such an image would have increased realism for the patient, but would be less relevant or consequential in their daily lives. FIG. 2 illustrates an exemplary facial expression composite image 200. It is important to note that with a line drawing as illustrated in FIG. 2, it is not possible to show the overlay of low and high frequency information; however, when taken in combination with the description herein, the skilled artisan will fully appreciate the concept.

In addition to composite images, ordinary photographs or illustrations of faces are another way to provide a test that utilizes the relevant interpretation of facial expressions. The preferred size of faces should be approximately 5 mm in height when viewed at 0.5 m and scaled appropriately to maintain this angular size for charts at different viewing distances. In addition to facial recognition, the image may preferably incorporate people of between 5 mm and 10 mm in height for a 0.5 m distance. Without correction these people may disappear into the background of the image.

Figure 3:
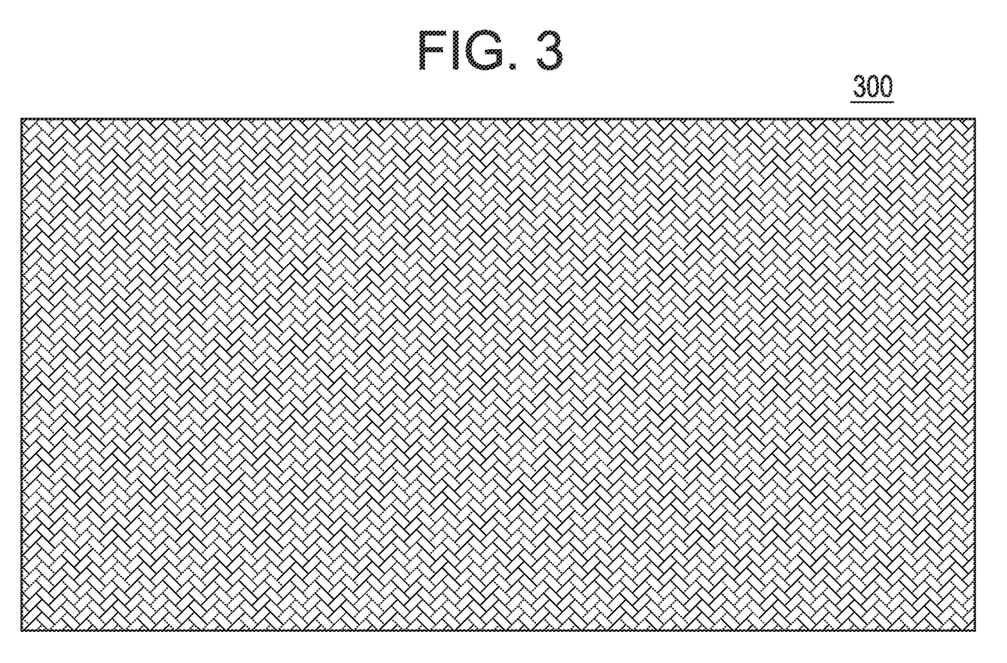
FIG. 3 is an exemplary high frequency image in accordance with the present invention.

Low levels of astigmatism or blur from other refractive errors make it more difficult to see the high frequency elements in an image and may cause them to disappear entirely when presented at low contrast. Accordingly, high frequency detail images may be utilized in accordance with the present invention to emphasize the difference. High frequency detail, including textural elements, will show significant changes in sharpness with correction of astigmatism. The difference will be even more noticeable if the textural elements only become visible to the patient once their vision is corrected because this creates a binary distinction. High frequency detail is important because textures and patterns make images more realistic and relevant to the individual's or patient's life, for example, seeing individual pebbles that form the surface of a sidewalk rather than a flat gray surface. High frequency detail is engaging because there is some freedom to create images that are interesting and fun for the patients, in addition to looking realistic. This may be best achieved with a portfolio of images from which one or both the eye care professional and the patient may choose. Pictures or images of the natural world may be utilized as examples of high frequency detail, such as leaves on distant trees or fur on animals. Patterns and weaves in fabric may also comprise a high frequency detail image. FIG. 3 illustrates an exemplary high frequency image 300.

Figure 4:
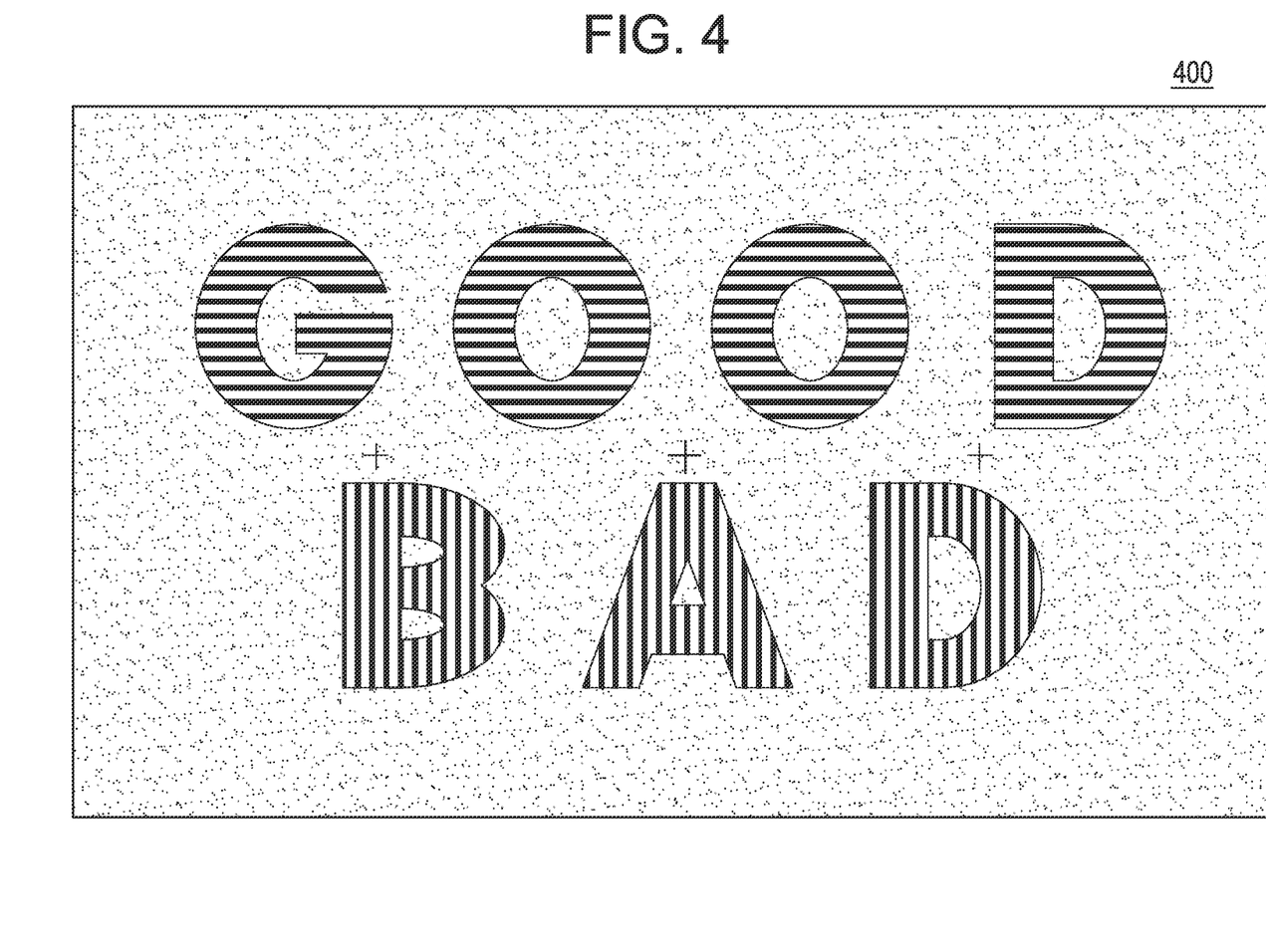
FIG. 4 is an exemplary grating and text image in accordance with the present invention.
Figure 5:
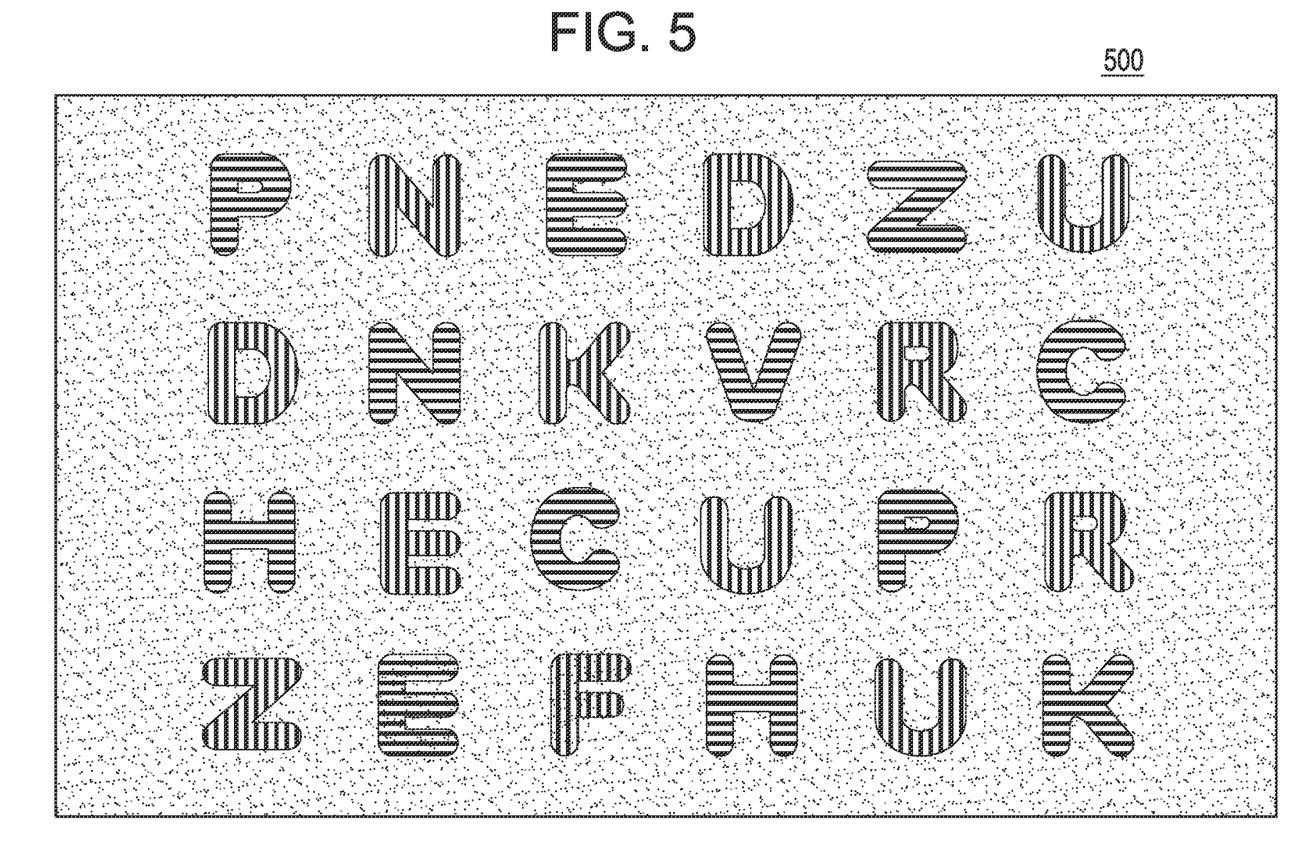
FIG. 5 is an exemplary rotating gratings image in accordance with the present invention.

Low levels of astigmatism make it more difficult to see gratings and text. A low contrast high frequency grating superimposed behind letters with the edges of the letters blurred to avoid the edge being overly apparent will cause an individual with low cylinder to see the letters disappear into the background when uncorrected. Gratings and text are noticeable because low contrast gratings are well known and often used to measure the contrast sensitivity function. The size and contrast of the grating may be tuned so that the letters completely disappear without correction and appear with correction, creating a strong binary difference. Gratings and text are not as relevant to daily life as other features disclosed herein; however, it is engaging in that the textual content of the image provides some opportunity to relate information that the patient finds fun and interesting. It is also possible to use the demonstration to help explain astigmatism, particularly the measurement of cylindrical axis. If the orientation of the grating in each letter is consistent with the patient's astigmatism, then they will only be able to read the word(s) or letter(s) once their vision is corrected. By orienting the gratings in different directions for different letters, some of the letters will not be visible without correction, while others would be. This change could be utilized to cause the patient to see one word or phrase without correction and a different word or phrase with correction. By making these sets of words or phrases having different meanings, the correction may be seen to have a significant and meaningful impact. FIG. 4 illustrates an exemplary gratings and text image 400. It is important to note that fiducial markers (+) are included in the image so that a patient may focus properly at the image plane, In a vision test that incorporates a rotating grating, to a patient with astigmatism, the stripes forming the grating will appear to pulsate as the grating rotates. With correction, the stripes will cease to pulsate and the patient will be able to observe clear gratings over the full range of rotation. This effect will work without modification for all axes of astigmatism. Rotating gratings are noticeable because the pulsating that patients see will be striking in of itself given that the eye is finely tuned to detect motion. The cessation of the pulsing when the patient corrects their astigmatism will thus create a significant and binary difference. While the rotating grating is noticeable, it has low relevance relating to importance and engagement. However, as before, it may be useful in the explanation of astigmatism, particularly the measurement of cylindrical axis. FIG. 5 illustrates an exemplary rotating gratings image 500. It is important to note that the single image as illustrated in FIG. 5 cannot show the rotation as described herein.

Figure 6:
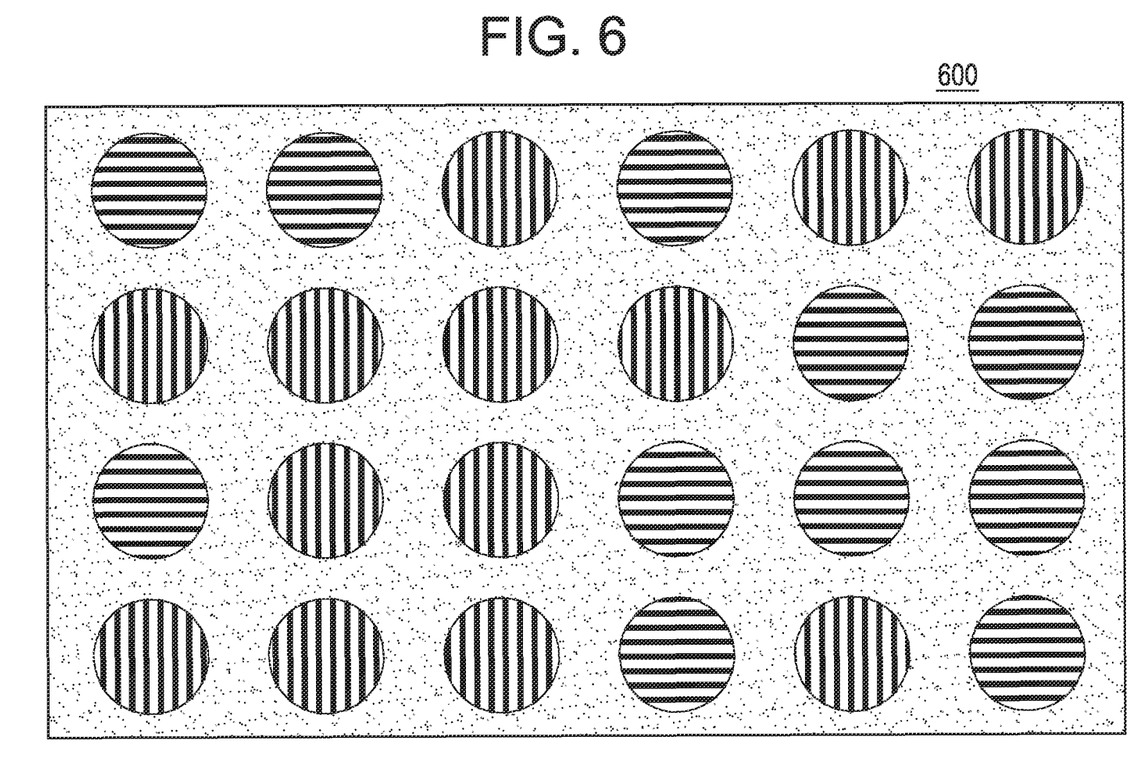
FIG. 6 is an exemplary array of gratings image in accordance with the present invention.

In a vision test that incorporates an array of low contrast, high frequency gratings, when the orientation of the grating matches with the patient's axis of astigmatism, the individual stripes blur together such that the individual stripes are no longer visible or identifiable. An array of gratings is noticeable because the disappearance of some of the gratings, but not others may emphasize the effect. There is a binary distinction between correction and no correction. It may also be possible to create a test within the test where the difference is measurable. The array of gratings is important because in allowing patients to see lines that they were not previously able to see, they may extrapolate that correction has a level of positive consequences on their vision. On their own, abstract images of lines will be less engaging than images with semantic meaning that incorporate lines as part of the image. There may be opportunities in both cases to increase engagement by incorporating the gratings into a real-life situation, such as shop signage, making the test interactive and/or utilizing it as an educational tool to explain astigmatism. FIG. 6 illustrates an exemplary array of gratings image 600.

Figure 7:
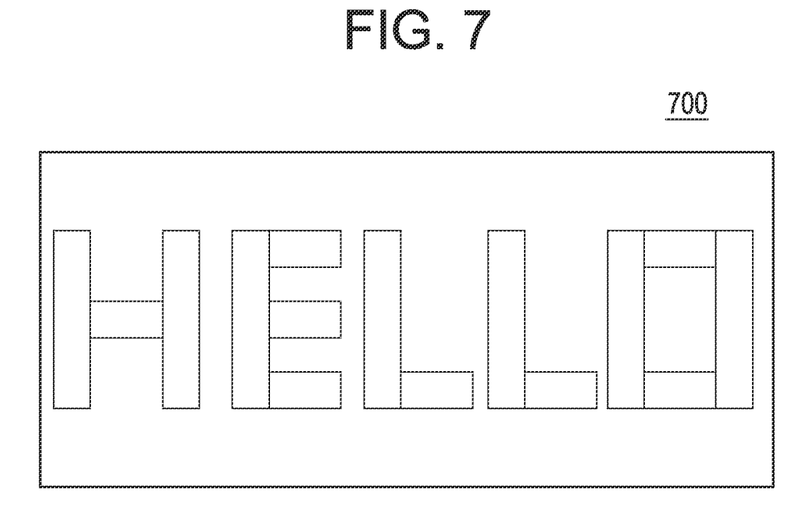
FIG. 7 is an exemplary line drawing in accordance with the present invention.

Line drawings and outline text composed mainly of narrow lines may be oriented in such a manner that some proportion or portion of the lines are oriented to match the patient's axis of astigmatism or cylinder axis. When the patient views the image without correction, parts of the image will blur or disappear entirely, and the specific parts that disappear will depend on the patient's astigmatism axis. Line drawings of this nature are noticeable because the blurring of a distinct part of an image creates an easily identifiable difference for the patient. By maintaining low contrast between the lines and the background of the image, it may be possible for some of the lines to disappear entirely. It may also be possible to design the images so that two different images are seen with and without correction. Line drawings are important because the content of the images/text may be tuned to the somewhat realistic and relevant. Once again, line drawings may be more engaging by creating drawings that relate to fun and interesting topics and a tool to educate on astigmatism. FIG. 7 illustrates an exemplary line drawing image 700.

Figure 8A:
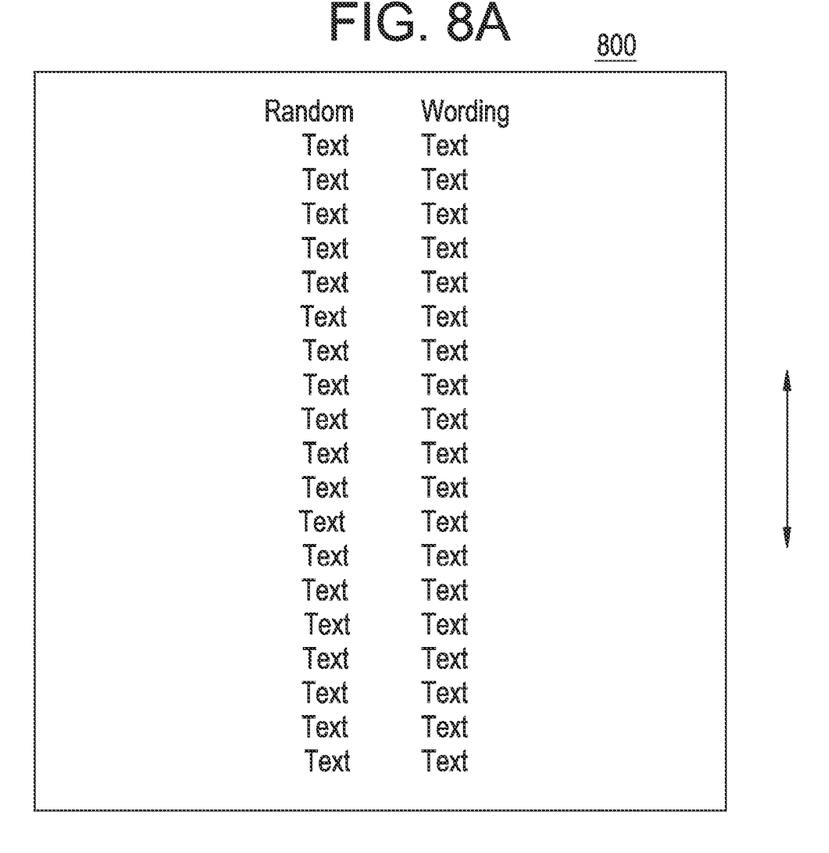
FIGS. 8A and 8B are exemplary scrolling text images in accordance with the present invention.
Figure 8B:
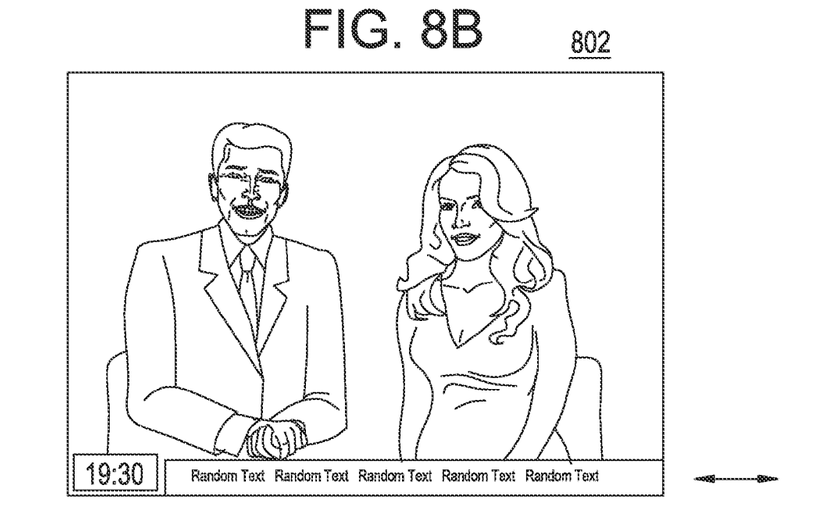

In a vision test that incorporates text in motion, a patient may be shown text that moves across a screen. This text may incorporate movie credits or the scrolling text along the bottom of the screen on a news, business, and/or sports channel. White on black text may make it even harder to read with astigmatism, as can varying color combinations. Text in motion is noticeable because the motion gives the patient less time to read the text, making high visual acuity more important. Correcting the patient's astigmatism will make the text noticeably easier to read. The text may even change from illegible to legible. The difference may also be made measureable, and thus quantifiable, by counting the number of lines of text that the patient correctly identifies each time. Moving text is important because it may be realistically related to several real-world scenarios, such as the movie screen credits, scrolling displays on news, business and/or sports channels, or moving or scrolling road signs, for example, traffic updates. The movement incorporated into these types of displays is engaging as they are likely to capture a patient's attention. Movement may also make the test more sensitive as the patient does not have the ability to fixate on one location and spend more time "blur interpreting." There is also a significant opportunity to make the test engaging through realistic videos and interactive test design. FIGS. 8A and 8B illustrate exemplary scrolling text. FIG. 8A is an exemplary depiction of the classic rolling credits 800 typically found at the end of a movie and FIG. 8B is an exemplary depiction of scrolling information 802 along the bottom of a television during a program. Once again, text in motion as described herein cannot be illustrated in a figure.

Text in perspective may be defined as text that is incorporated into an image that shows depth. This text in perspective may be a sign on the side of a building that gets smaller as it goes further from the viewer, or it may be the difference between two (2) signs positioned normally to the viewer, at different apparent distances in the image. The range of sizes that may be included accommodate a range of patients and their differing visual acuities. The relative size of the text may be related to a real world situation, for example, like reading a shop or road sign from a block away, and the text may be at an angle relative to the scene and possibly less dependent on the orientation of the astigmatism or cylinder axis. An image in accordance with the present invention includes text in perspective. Text in perspective is noticeable because the text is sized such that high visual acuity is typically required to read it and a set of characters typically cover a range of spatial frequencies and orientations. It is for this reason that visual acuity changes with astigmatic blur, but the use of perspective allows for text to be put in context in a real world scenario, and for that text to be at varying angles from the viewer. Correcting the patient's astigmatism will improve the clarity of the text, making it easier to read. It may be possible to tune the image so that some text changes from illegible to legible. The difference may also be made measurable, and thus quantifiable, by comparing the size of the smallest text that is readable each time. Text in perspective is important because the perspective in the image is used to relate the text in a convincing way to a real world situation, for example, reading supermarket signs from the end of the isle, and provides a clear indication of how astigmatism negatively affects their vision and daily activities. The text in perspective is engaging because of the richness and realism and the relevance of these images may capture the patient's attention. Another advantage of text in perspective is that the spatial frequencies of the text in different directions may be varied independently. For example, orienting the text on the side of a building such that it has a high aspect ratio from the perspective of the viewer will increase the horizontal spatial frequency, but with no significant impact to the vertical spatial frequency.

Figure 9:
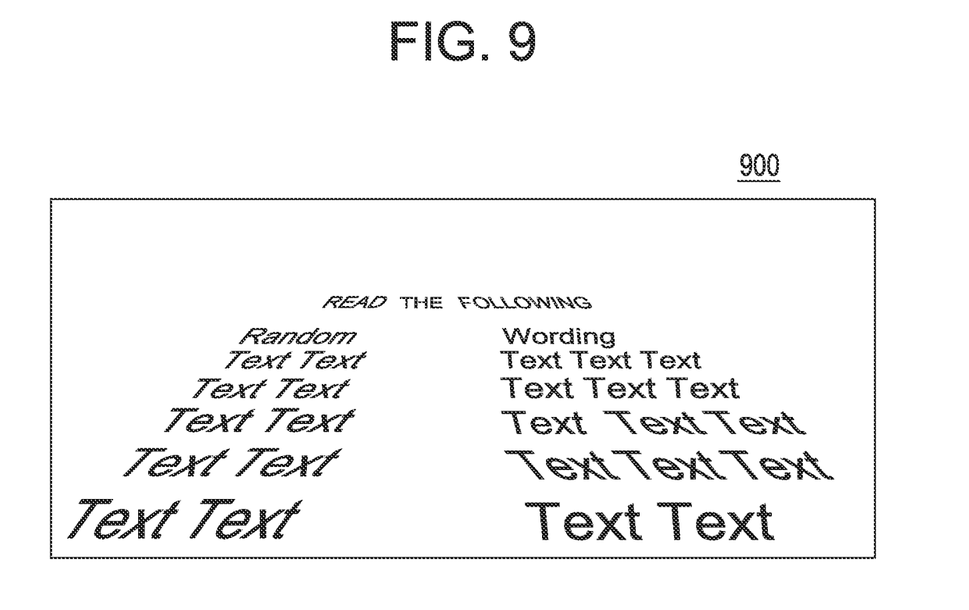
FIG. 9 is an exemplary text in perspective image in accordance with the present invention.

In order to give the image a real sense of scale, context and visual cues are preferably provided. The image preferably comprises a vanishing point, which may or may not be in the frame of the image, a depth of field, a field of view and reference objects. The vanishing point helps to relate the foreground to the background and indicate the total depth of the image. A deep depth of field helps give the illusion of depth on a flat image when image details are sharp throughout, such as with astigmatism correction. Human eyes on average have a field of view between one hundred twenty (120) and one hundred fifty (150) degrees, so it is important that the image have a wide field of view to be engaging. Limitations of print/display size and viewing distance may impact the ability to display full eye field of view, but larger fields are more likely to be engaging for the subject. A reference guideline from the motion picture industry suggests a minimum of a twenty-six (26) degree field of view for movie theaters to maintain an engaging experience. Reference objects have assumed heights, for example, people and doors, which help the viewer to assess dimensions in the image. With an image having text in perspective, an individual or patient with correction should be able to read text deeper into the image. FIG. 9 illustrates a text in perspective image 900.

Figure 10:
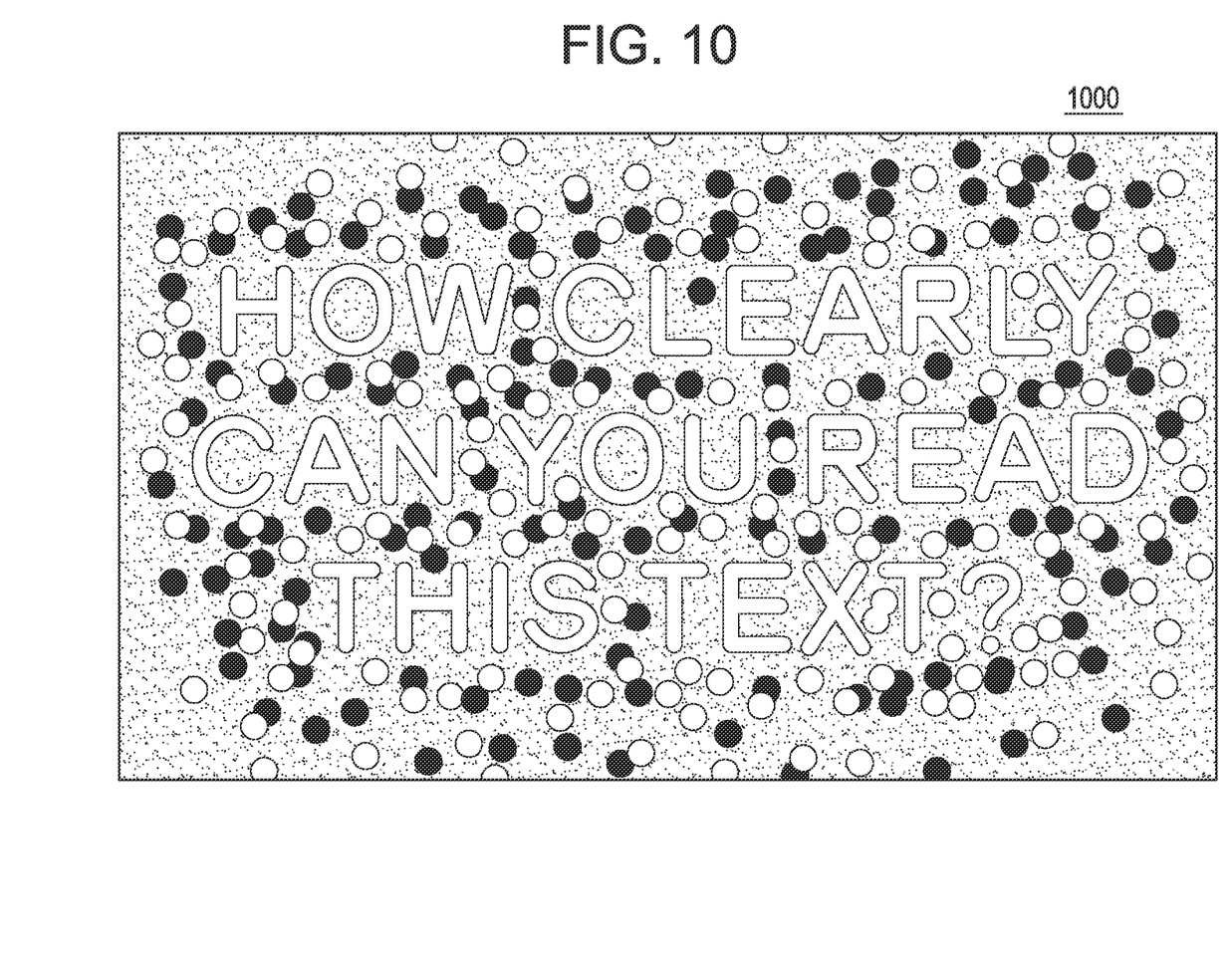
FIG. 10 is an exemplary text with distraction image in accordance with the present invention.

Text with distraction also provides a valuable means for demonstrating the value of low cylinder astigmatism correction. Text with additional patterns around, over or under the letters is much harder to read in the presence of low levels of astigmatism. This is most likely due to the fact that the patterns around the text blur into the letters and increase the visual acuity required to resolve the edges, and the high superfluous information content around the letters distracts the brain from reading the text. The distraction patterns around text may also reduce the local contrast in different ways around each letter, including reducing or eliminating the gaps in letters such as the "hole" formed by the loop in a lower-case "e", which makes letter detection even more difficult. Text with distraction is noticeable because the addition of the distractions increases the magnitude of the difference that the patient sees between with and without corrections, as compared with text on its own. This form of vision test is highly relevant to real world advertising and shop signage, which can consist of words overlaid on images or logos. Also glare over a reflective sign, or sign behind glass, can create distraction for text. Additional distraction elements may include rain and snow. The text with distraction may be made engaging by integration into the image in advertising, signage, and glare in a real world scene. FIG. 10 illustrates an exemplary text with distraction image 1000.

Figure 11:
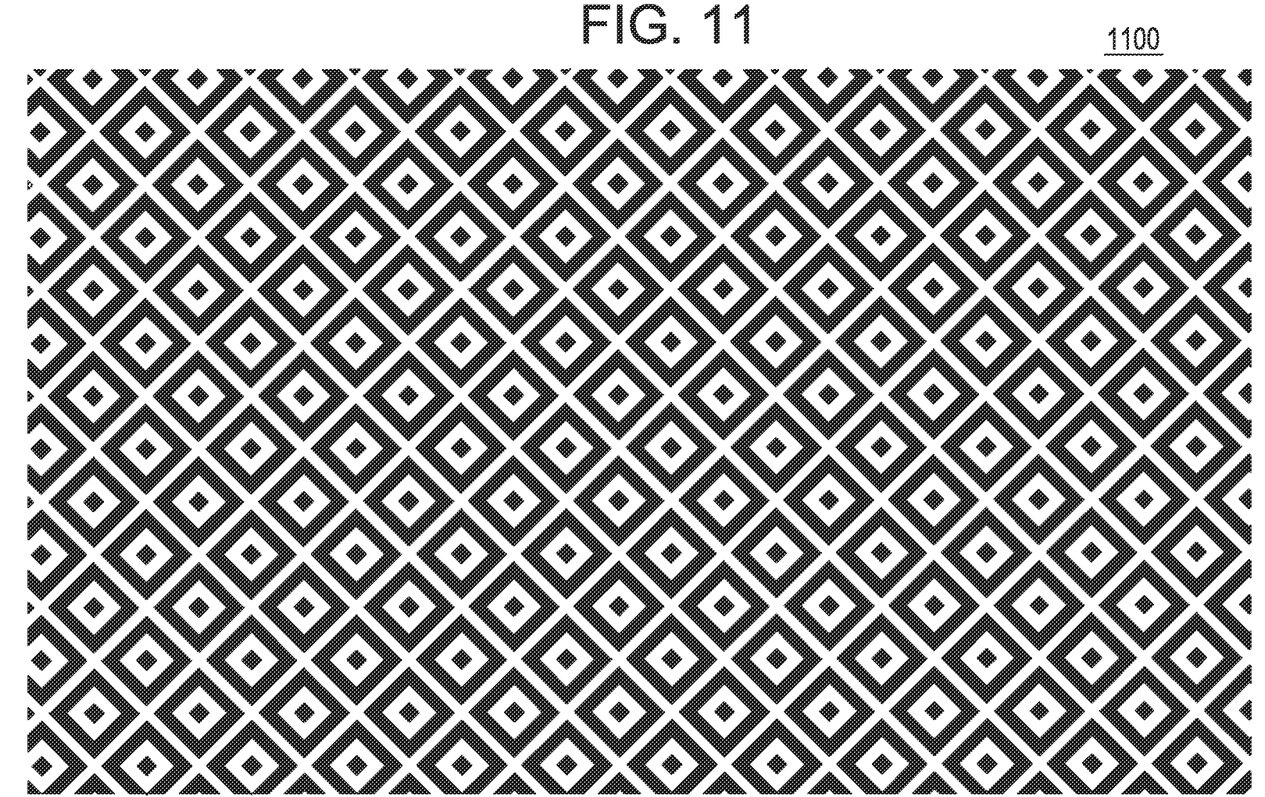
FIG. 11 is a high contrast pattern image in accordance with the present invention.

High contrast patterns may be utilized in accordance with the present invention in a reverse case scenario. In the typical high contrast pattern scene, it was found that the introduction of a one (1) diopter cylinder, observed from the appropriate distance, may make the image appear, in other words, you see the image without correction. Accordingly, the present invention may utilize a distracting texture behind a black pattern and asking the patient to focus on the clarity of the black pattern. A high contrast pattern is noticeable because it may appear quite murky through a low level of astigmatism, but vivid and crisp with perfect correction. A grey pattern under the black pattern seems to add confusion to the defocus of the black stripes, enhancing the effect. With correction; however, the black stripes become clear and crisp, and the gray pattern disappears. While this test is fairly abstract, it is believed to be important given that the patient appreciates the noticeable effect, the improved crispness of the lines, and the implied benefit for their vision more generally. If the image is tuned correctly, the appearance/disappearance of the low contrast image or pattern under the high contrast pattern may be quite surprising and thus engaging. In accordance with one exemplary embodiment, it may also be possible to design the image such that information regarding the use of toric lenses may be conveyed to a patient. For example, the information may reveal a message telling them that their eyesight may be improved with toric lenses. FIG. 11 illustrates a high contrast pattern image 1100.

The eye exam in accordance with the present invention may be administered in any suitable manner, for example, in a doctor's office or in any other controlled environment including an individual's home. The test may be administered virtually, for example, delivered over the internet to a home computer, smartphone, or tablet. A simple flipper tool, as illustrated in FIG. 1, may be utilized with adaptive lenses to correct the low cylinder astigmatism. It is also important to note that the charts/images disclosed herein may be selected for a particular patient's interest. Essentially, the charts may be customized to regions, activities, groups or genre, for example, sports. A computer based text might allow automatic customization to a patient's prescription or changing the language of text to the patient's native language. The test may be presented on a wide range of media, including a printed booklet for viewing in the near-field, a large wall poster for viewing at a distance, a public display, a complex monitor or projector for viewing at a distance, a tablet screen for viewing in the near field. The choice of medium will also depend on whether motion or interactivity is required. Interactivity includes augmented reality and interactive games/tests.

It is important to note that if a computer monitor or tablet is utilized, it should preferably have a high resolution display. Without a high resolution display there will not be a high enough pixel density to display the required spatial frequencies.

A meaningful demonstration to one person may be irrelevant to another person. Accordingly, the present invention may comprise a portfolio of scenes from which the doctor or patient may select. This portfolio would preferably cover a range of prescriptions and visual acuities as well as a range of interests. The doctor may ask the patient about any interests, or the patient may browse through the portfolio. A computer based test may allow automatic customization to a patient's prescription as well as his or her interests.

Regardless of the particular image or the medium, the result of correction should appear clearer, sharper and richer.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for demonstrating the benefits of correcting blurred vision, the method comprising the steps of:
   presenting a composite image to a patient with a low level of astigmatism, the composite image comprising a scene composed of textual and non-textual elements and having a number of properties, including facial recognition and expressions, high frequency detail, gratings and text, rotating gratings, array of gratings, line drawings, text in motion, text in perspective, text with distraction, and high contrast patterns;
   assessing the patient's reaction to the presented image without blurred vision correction; and
   re-assessing the patient's reaction to the presented image with blurred vision correction to demonstrate the effect of vision correction for patients with low levels of astigmatism.

* * * * *